United States Patent
Schmainda et al.

(10) Patent No.: US 8,670,602 B2
(45) Date of Patent: Mar. 11, 2014

(54) MULTIPARAMETER PERFUSION IMAGING WITH LEAKAGE CORRECTION

(75) Inventors: Kathleen Schmainda, Elm Grove, WI (US); Eric S. Paulson, Jackson, WI (US); Douglas E. Prah, Milwaukee, WI (US)

(73) Assignee: Imaging Biometrics, LLC, Elm Grove, WI (US)

( * ) Notice: Subject to any disclaimer, the term of this patent is extended or adjusted under 35 U.S.C. 154(b) by 592 days.

(21) Appl. No.: 12/601,241

(22) PCT Filed: May 22, 2008

(86) PCT No.: PCT/US2008/064597
§ 371 (c)(1),
(2), (4) Date: May 24, 2010

(87) PCT Pub. No.: WO2008/147921
PCT Pub. Date: Dec. 4, 2008

(65) Prior Publication Data
US 2010/0296714 A1 Nov. 25, 2010

Related U.S. Application Data

(60) Provisional application No. 60/939,539, filed on May 22, 2007.

(51) Int. Cl.
*G06K 9/00* (2006.01)
*A61B 5/05* (2006.01)

(52) U.S. Cl.
USPC ............ 382/128; 382/130; 382/131; 600/410

(58) Field of Classification Search
USPC .......................... 382/128–131; 600/410, 431
See application file for complete search history.

(56) References Cited

U.S. PATENT DOCUMENTS

| | | | |
|---|---|---|---|
| 6,792,302 B2 | 9/2004 | Wintermark et al. | |
| 6,807,441 B2 | 10/2004 | Schmainda | |
| 2006/0034765 A1 | 2/2006 | Schmainda et al. | |
| 2008/0221441 A1* | 9/2008 | Bjornerud et al. | 600/425 |
| 2010/0030071 A1* | 2/2010 | Wu et al. | 600/431 |
| 2010/0069739 A1* | 3/2010 | decharms | 600/410 |

OTHER PUBLICATIONS

E.S. Paulson et al., Compensation of Confounding T1 and T2 Dipolar and Residual Susceptibility Effects in DSC-MRI Using Dual-Echo Spiral; Proc. Intl. Soc. Mag. Reson. Med.; 2007; 15:2811.
C. C. Quarles et al., Quantitative Assessment of Tumor Perfusion and Ktrans Using Dual-Echo DSC-MRI Signals Compensated for Extravascular Tissue T1 and T2 Relaxation; Proc. Intl. Soc. Mag. Reson. Med.; 2005; 13:2099.

(Continued)

*Primary Examiner* — Luke Gilligan
(74) *Attorney, Agent, or Firm* — Glenn H. Lenzen; Husch Blackwell LLP

(57) ABSTRACT

A magnetic resonance imaging (MRI) methodology is provided for simultaneous measurement of dynamic susceptibility contrast (DSC) MRI and dynamic contrast enhanced (DCE) MRI perfusion and permeability parameters using a combination of dual echo and spiral acquisition techniques with no contrast agent preload. T1 and T2/T2* leakage effects are eliminated, thereby permitting accurate measurement of blood volume, blood flow and vascular permeability which are used in evaluating tumor angiogenesis.

21 Claims, 9 Drawing Sheets

TUMOR

(56) References Cited

OTHER PUBLICATIONS

Leif Ostergaard, Principles of Cerebral Perfusion Imaging by Bolus Tracking; J. Magn. Reson. Imaging; 2005; 22:710-717.
EPO Search Report for European Application No. 08769657.1 dated Feb. 24, 2012.
Provenzale et al., Correlation of Relative Permeability and Relative Cerebral Blood Volume in High-Grade Cerebral Neoplasms, American Journal Roentgenology, Oct. 2006; vol. 187, 1036-1042, See p. 1036, lines 4-33.
PCT/US08/064597—International Search Report and Written Opinion dated Oct. 29, 2008.

* cited by examiner

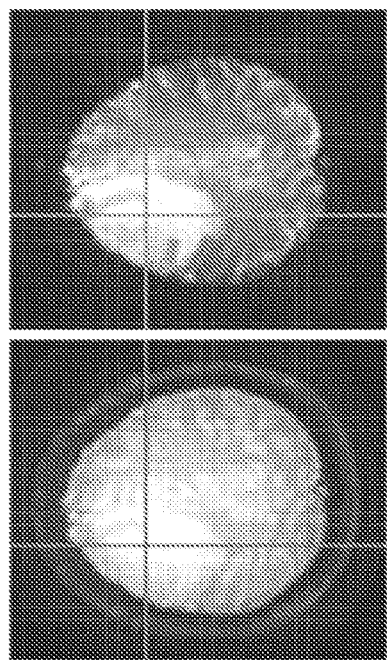
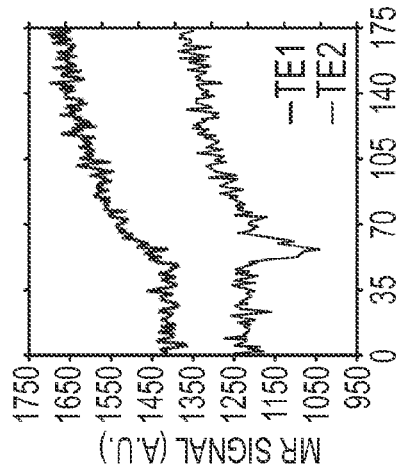
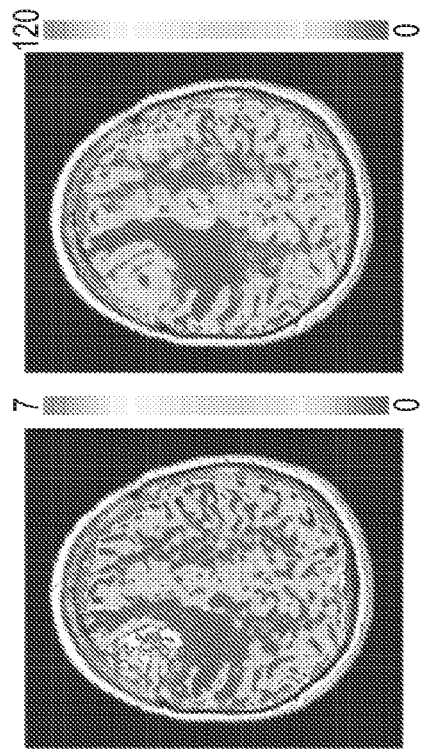
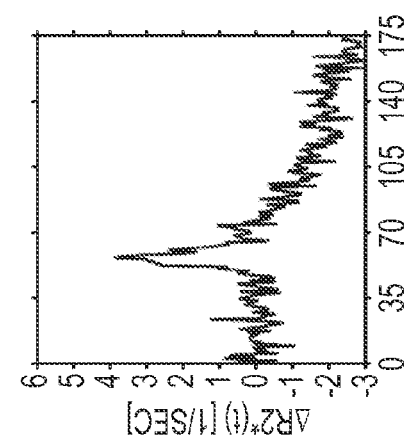
FIG. 2A
FIG. 2B FIRST ECHO IMAGE
FIG. 2C SECOND ECHO IMAGE
FIG. 2D
FIG. 2E NORMALIZED rCBV (A.U.)
FIG. 2F CBF (ml/100ml/MIN)

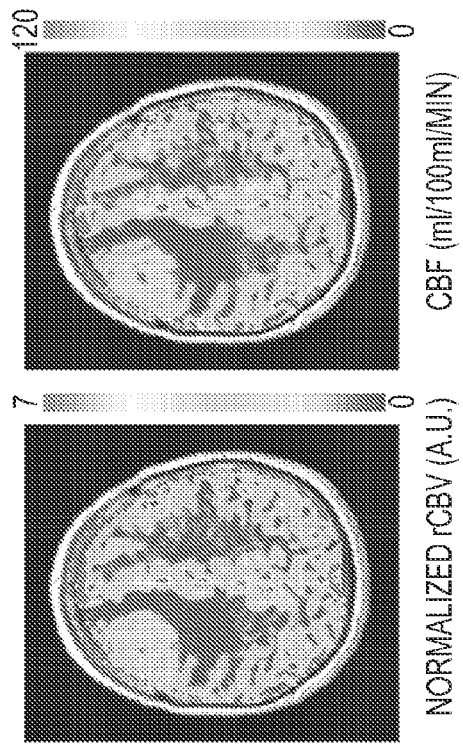
FIG.2G
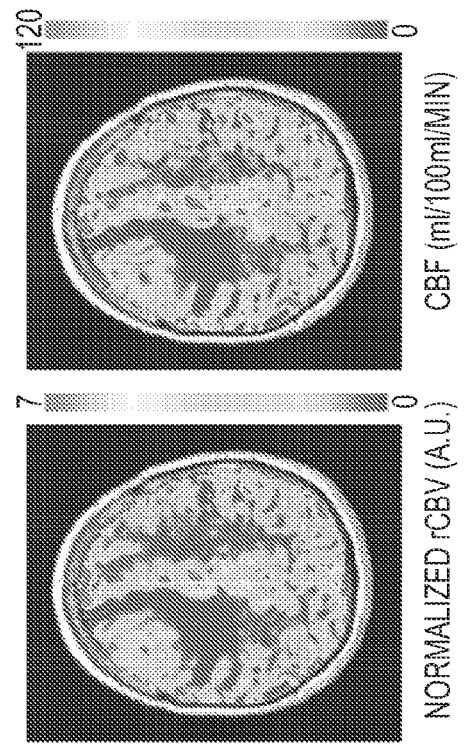
FIG.2H
FIG.2I
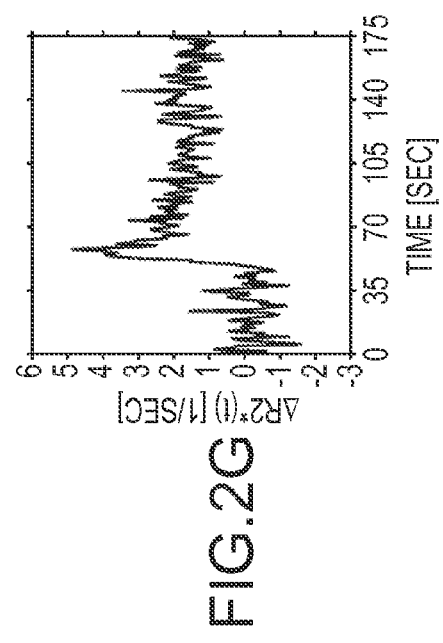
FIG.2J
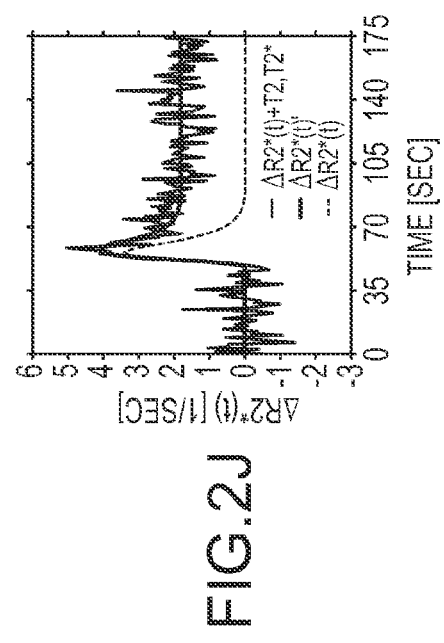
FIG.2K
FIG.2L

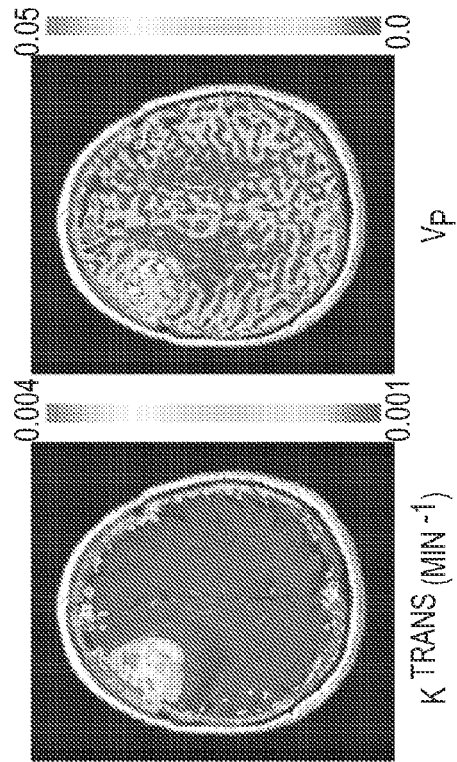
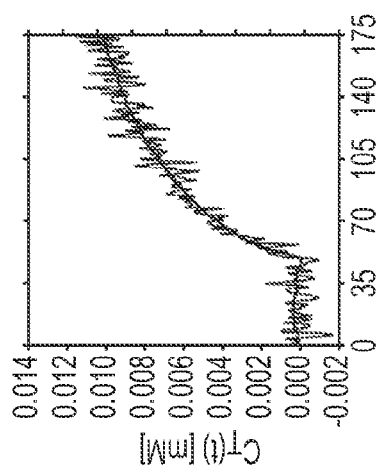
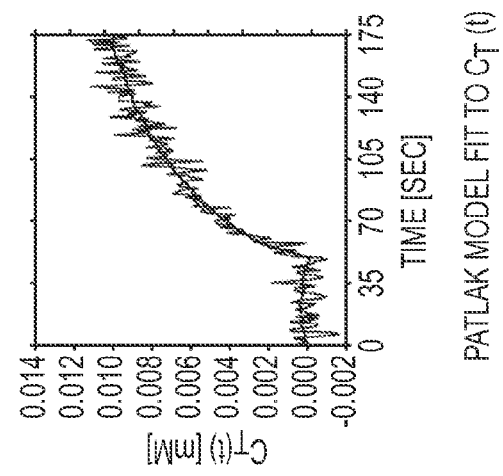
FIG.3A  FIG.3B  FIG.3C
FIG.3D  FIG.3E  FIG.3F

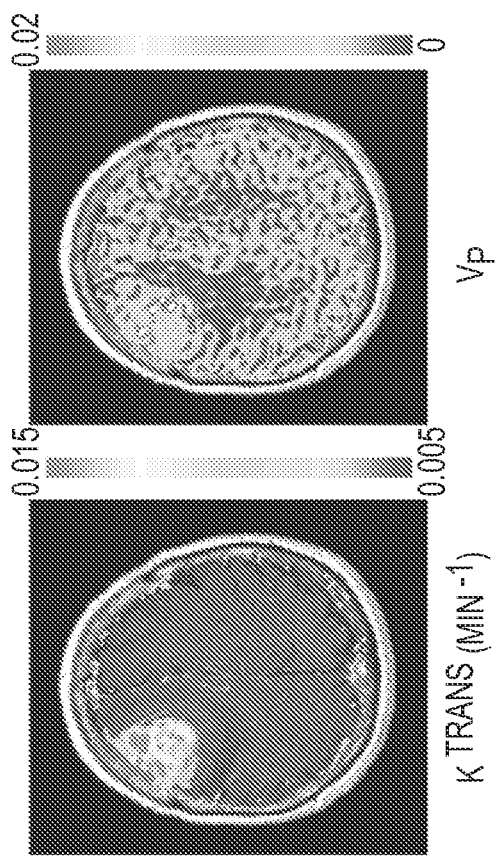
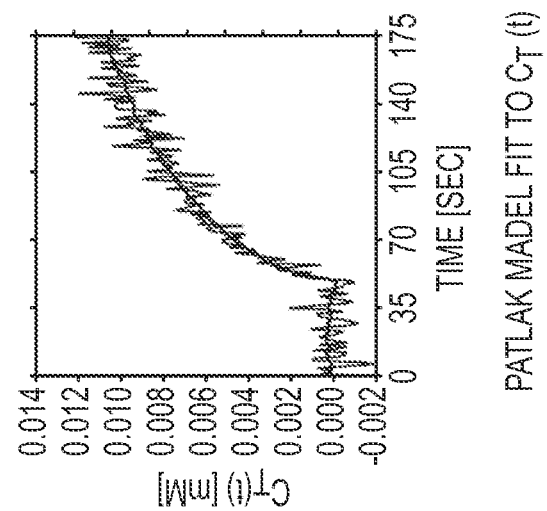
FIG. 3G  FIG. 3H  FIG. 3I

ARTERY

TUMOR

MULTIPARAMETER PERFUSION IMAGING WITH LEAKAGE CORRECTION

CROSS-REFERENCE TO RELATED APPLICATIONS

This application is the National Stage of International Application No. PCT/US2008/064597 filed May 22, 2008, which claims the benefit of U.S. Provisional Patent Application Ser. No. 60/939,539 filed on May 22, 2007.

BACKGROUND OF THE INVENTION

Magnetic resonance imaging (MRI) relies on the relaxation properties of excited hydrogen nuclei in water and lipids to create images. When the target object to be imaged is placed in a uniform magnetic field, the forces in the magnetic field cause the spins of atomic nuclei having a non-zero spin to align in a particular manner with the applied magnetic field. By way of example, hydrogen atoms have a simple spin (1/2) and therefore align either parallel or anti-parallel to the magnetic field. A radio frequency pulse (RF) is then applied in a direction perpendicular to the magnetic field and removed. When the RF signal is removed, the atomic nuclei relax. During the relaxation process, the nuclei release energy by emitting an RF signal unique to the nuclei, which may be measured by a conductive field coil placed around the target object. This measurement is processed or reconstructed to obtain the magnetic resonance images.

The signal intensity of a given tissue type depends upon the density of the protons in the tissue. However, the contrast of the image also depends on two other tissue-specific parameters: the longitudinal relaxation time (T1) and the transverse relaxation time (T2). T1 defines the time required for the displaced nuclei to return to equilibrium, that is to say, the time required for the nuclei to realign themselves in the magnetic field. T2 is the time required for the signal emitted by a specific tissue type to decay.

Image contrast is created by using a selection of image acquisition parameters that weights signals by T1, T2 or T2*, or no relaxation time, which are known in the art as proton density images. For example, in the brain, T1-weighting causes the nerve connections of white matter to appear white, and the congregations of neurons of gray matter to appear gray. Cerebrospinal fluid appears dark.

Dynamic Susceptibility Contrast (DSC) MRI and Dynamic Contrast Enhanced (DCE) MRI are two minimally-invasive imaging techniques frequently employed to probe the angiogenic activity of brain neoplasms based on estimates of vascularity and vascular permeability. Contrast agents may be used to enhance tissue contrast in MRI images by inducing susceptibility contrast effects when injected. Most commonly, a paramagnetic contrast agent, typically a gadolinium compound is employed for this purpose; although, as will be discussed in greater detail below, several different contrast agents may also be used. Gadolinium-enhanced tissues and fluids appear extremely bright in T1-weighted images, thereby providing high contrast sensitivity which facilitates the detection of vascular issues (tumors) and permits assessment of brain perfusion, such as that which occurs following a stroke. Cerebral blood volume (CBV) and cerebral blood flow (CBF) can be measured, and other hemodynamic and vascular parameters can be derived from these measurements. However, a significant problem associated with the use of gadolinium-based contrast agents is that they leave or leak from the blood vessels. This leakage results in undesirable T1 and T2 relaxation effects that confound the measurement of perfusion.

Efforts to correct contrast leakage effects on measurements for rCBV are discussed in U.S. Pat. No. 6,807,441 B2 issued on Oct. 19, 2004, and in U.S. Patent Application Publication No. US2006/0034765 A1 published on Feb. 16, 2006. These disclosures entail the use of gradient-echo and spin-echo NMR signals and either a ΔR2 weighing ratio or the T2* and T2 relaxation rates to measure tumor angiogenesis.

However, the results of both DSC- and DCE-MRI may be confounded by the opposing effects of gadolinium. While necessary for the DCE-MRI technique, the shift in compartmental distribution of the contrast agent from the intravascular space to the EES results in T1 shortening effects that compete with the susceptibility-induced signal dropout, which can confound DSC-MRI signal time courses. The most well characterized DSC-MRI parameter affected by T1 leakage effects is rCBV.

Accordingly, a need exists for a method of measure and assessing the hemodynamic properties of a tumor where extravasation of a contrast agent is present, not only in brain tumors where the blood-brain barrier may be disrupted by disease, but also in tumors present in other parts of the body where extravasation may be present.

SUMMARY OF THE INVENTION

The present invention addresses the afore-mentioned and other problems by providing a new and useful MRI methodology which uses a combination of dual-echo acquisition and single shot SPIRAL acquisition to eliminate T1 leakage effects and post-processing algorithms to eliminate T2/T2* effects resulting from contrast agent leakage, thereby permitting accurate and robust measures of blood volume and flow, as well as vascular permeability. Moreover, tissue perfusion outside of the brain, such as in and around cancers of the breast, prostate, and musculoskeletal system may be measured. Organ perfusion may also be measured in other normal and disease states as well, including but not limited to organ transplants, sickle cell disease and diabetes. The technique herein disclosed may also be applied to studies related to the development and testing of drugs and may preclude the need for a loading dose of Gd contrast agent, thus decreasing the cumulative dose needed for each patient's study.

The methodology of the present invention permits the calculation of vascular permeability using well-know T1-based modeling algorithms. No other technology enables the collection of both T2/T2* perfusion data and T1-based permeability data at the same time.

BRIEF DESCRIPTION OF THE DRAWINGS

FIG. 2(a)-(l) are examples of dual-echo correction of DSC-MRI data and corresponding images of a brain according to an embodiment;

FIGS. 3(a)-(i) illustrate dual-echo correction of DCE-MRI data;

DESCRIPTION OF THE PREFERRED EMBODIMENT

Figure 1A:
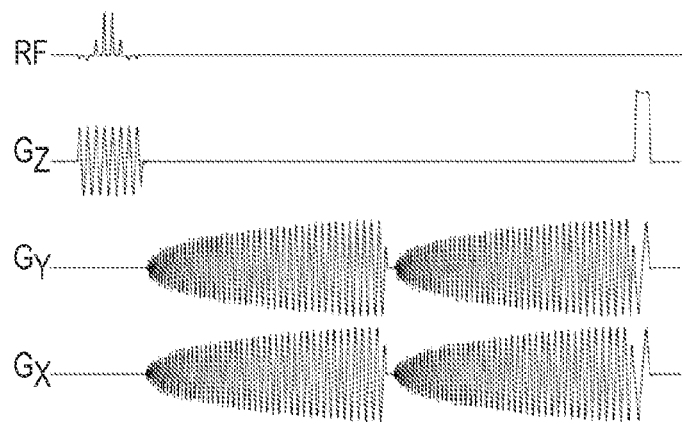
FIG. 1(a) is an example of a single shot, dual echo, spiral out MRI pulse sequence according to an embodiment.

Dynamic Susceptibility Contrast (DSC) MRI and Dynamic Contrast Enhanced (DCE) MRI are two minimally invasive imaging techniques frequently employed to probe the angiogenic activity of brain neoplasms based on estimates of vascularity and vascular permeability. It is well known that gadolinium produces simultaneous T1, t2, and T2* shortening effects in tissue, and these properties are uniquely exploited in DSC- and DCE-MRI. However; several different MRI contrast agents are capable of inducing susceptibility contrast effects when injected. Therefore, several different contrast agents can be used in conjunction with the described invention. Most commonly, paramagnetic agents such as Gd (gadolinium)-chelated contrast agents are used. When Gd(III)-chelated agents are injected quickly, under bolus-like conditions, they induce susceptibility contrast in tissues, notable as a transient decrease in a T2 or T2*-weighted MRI signal. Alternatively, another category of contrast agents can be used. These agents are superparamagnetic iron-oxide contrast agents, such as MION (monocrystalline iron oxide nanoparticles), or USPIO (ultra-small polycrystalline nanoparticles). These agents can also cause the necessary susceptibility contrast for this invention.

In DSC-MRI, a concentrated bolus of gadolinium, confined to the intravascular space and flowing through a tissue capillary bed, induces transient signal loss through spin dephasing caused by vascular-extravascular susceptibility gradients. So long as recirculation effects are eliminated, analysis of DSC-MRI data, using indicator dilution theory provides hemodynamic estimates of relative cerebral blood volume (rCBV), cerebral blood flow (CBF), and mean transit time (MTT). In DCE-MRI, contrast agent extravasation, arising from disruptions of the blood-brain barrier, gives rise to signal enhancement through dipolar inter-action between gadolinium's unpaired electrons and local tissue protons. Pharmacokinetic analysis of DCE-MRI data provides insight into the underlying tissue pathophysiology, through estimation of the blood-brain volume transfer constant ($K^{trans}$), fractional extravascular, extracellular space (EES) volume (Ve), and the efflux rate constant from EES to plasma (Kep).

Dual-echo MRI acquisition methods offer a robust alternative to single-echo acquisitions following loading doses when collecting DSC-MRI data, in brain tumor patients. According to an embodiment of the present invention, it has been demonstrated that brain tumor vascularity and vascular permeability parameters, corrected for confounding contrast agent leakage and recirculation effects, can be obtained simultaneously with a dual-echo acquisition using a standard dose of contrast agent. There are several differences between the method herein disclosed and previous prior art methods. First, in addition to correcting DSC-MRI parameters for T1 leakage effects, both DSC- and DCE-MRI parameters are corrected for residual susceptibility effects and T1/T2* effects arising from contrast agent recirculation and leakage. A formalism for the correction of both DSC- and DCE-MRI parameters in accordance with the present invention is presented in the Appendices. Second, the method herein disclosed facilitates estimation of corrected DSC- and DCE-MRI parameters using conventional algorithms found in the literature. Third, a pre-load or loading dose of contrast agent is no longer required to estimate DSC-MRI parameters in regions of tumor. Fourth, pre-contrast $S_0$ and T1 calibration scans, traditionally required for DCE-MRI analysis, have been eliminated. Finally, a spiral approach, which encodes two echoes simultaneously within an employed for the dual-echo acquisition.

Data Acquisition

Images were acquired on a 1.5 T GE CV scanner (GE Healthcare, Milwaukee, Wis.), running software version 12.0, equipped with 40 mT/m gradients (150 T/m/s slew rate), and using a, commercial quadrature RF coil. The basic system configuration and operation are disclosed in the '441 patent and '765 publication cited above and are incorporated herein by reference. Pre-contrast FLAIR, DWI, T1, and T2 images were collected as part of the standard clinical protocol. Perfusion-weighted images were then acquired using a custom, single-shot, dual-echo, FID spiral-out sequence with the following parameters: FOV=22 cm$^2$, matrix=96$^2$. $TE_2$=2.6 msec, $TE_2$=41 msec, TR=1350 msec, θ=72 degrees, slice thickness=5 mm, skip=1.5 mm, number of slices=13, number of samples (reps)=180. A 30 second delay was inserted between prescan and the beginning of the dual-echo acquisition to allow full recovery of longitudinal magnetization. This facilitated estimation of the equilibrium magnetization from the first time point of the dual-echo acquisition and eliminated the necessity of collecting a separate pre-contrast calibration scan (see Appendix B). A standard dose of Gadodiamide (0.1 mmol/kg, Omniscan) was injected at 3 mL/sec using a power injector 60 seconds after the start of acquisition. Post-contrast T1W images were then acquired as part of the standard clinical protocol.

As shown in FIG. 1a, the pulse sequence acquired two echoes sequentially within a free induction decay (FID) immediately following a spatial-spectral excitation pulse, which was used to reduce the chemical shift influence on off resonance effects through selective excitation of water. Steady-state signal incoherency was established by applying a killer pulse to spoil the transverse magnetization before acquisition of each subsequent shot. To reduce nonlinearities resulting from gradient warming, the killer was applied along the slice select axis, since this axis had the lowest gradient duty cycle.

The Ernst angle (72 degrees) was chosen to maximize the signal-to-noise ratio of the dual-echo acquisition in an effort to prevent the second-echo signal, particularly in large vessels, from saturating at the rectified noise floor during the first pass of the bolus. Saturation of the signal can result in nonlinearities in the relationship between signal changes and contrast agent concentration, which can introduce error in the estimate of the arterial input function.

The spiral gradient waveforms were implemented using the Glover approach, as is known in the art. Although reversed spiral readouts would have produced better edge definition, the spiral-out direction was chosen to increase the signal to noise ration SNR, and minimize the TE of the first echo in order to maximize T1 weighting for DCE-MRI parameter estimation. For a 96×96 matrix, the spiral waveforms consisted of 3892 points corresponding to a readout duration of approximately 38 msec. Although insignificant for single-shot spiral, hysteresis correction gradients were implemented to reduce artifacts associated with gradient amplifier current monitor hysteresis. In dual-echo acquisitions, the first echo readout results in an apparent diffusion weighting for the second echo. The amount of diffusion weighting is characterized by the b-value, calculated using:

$$b = \gamma^2 \Delta t^3 \sum_{i=1}^{N} \left[ \sum_{j=1}^{i} G_j \right]^2 \quad (1)$$

where G is the spiral readout gradient waveform, y is the gyromagnetic ratio, and $\Delta t$ is the gradient update time (4 μsec for scanner employed in the test). For the gradient waveforms used in the present study the b-value was estimated to be 0.0123 s/mm².

Data Analysis

Figure 1B:
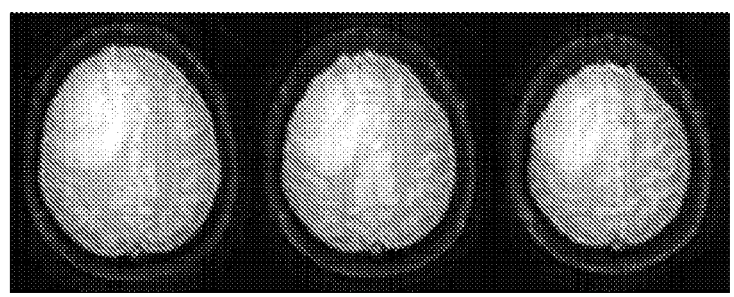
FIGS. 1(b) and 1(c) are reconstructed echo images of a brain tumor according to an embodiment.
Figure 1C:
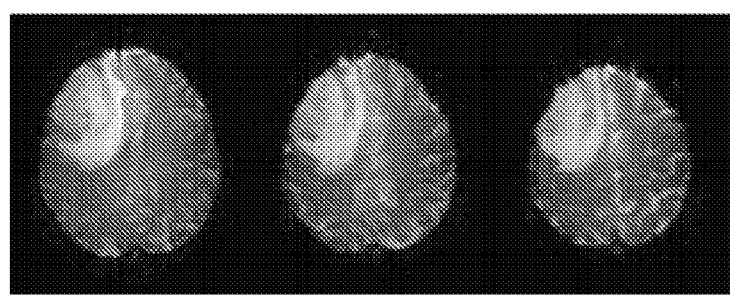

The raw spiral data was transferred to a remote Linux workstation (quad AMD dual-core 2.4 GHz CPUs, 16 GB RAM, SUSE 10.3) and reconstructed offline using custom Matlab (Version 7.5. R2007b, The MathWorks, Inc.) software. Sample reconstructed spiral images from the first- and second echoes are displayed in FIGS. 1b-c.

DSC-MRI

Simple algebraic derivations for DSC-MRI concentration-time curves without and with correction for confounding leakage effects can be found in Appendix A. For comparison of the new and novel method of the instant invention to conventional methods, three versions of $\Delta R2^*(t)$ concentration-time curves were generated and used in the analysis: 1) $\Delta R2^*(t)$ generated using the second-echo signal of the dual-echo acquisition (equation 19), 2) $\Delta R2^*(t)$ generated using the ratio of the dual-echo signals (equation 34), and 3) $\Delta R2^*(t)$ generated using the ratio of the dual-echo signals and corrected for recirculation and any additional T2/T2* leakage effects (equation 36). After truncating the $\Delta R2^*(t)$ curves to remove signal transients during the approach to steady-state, DSC-MRI parameters were estimated using conventional DSC-MRI algorithms. The arterial input function (AFI) was generated by averaging the $\Delta R2^*(t)$ time courses from three voxels manually selected in regions of the middle cerebral arteries. Estimates of rCBV were obtained using:

$$rCBV = \frac{k_h}{\rho} \frac{\int_0^\infty \Delta R_2^*(\tau) d\tau}{\int_0^\infty AIF(\tau) d\tau} \quad (2)$$

where ρ is the density of brain tissue (1.04 g/ml) and $k_h$ is a correction factor for the difference in large versus small vessel hematocrit:

$$k_h = \frac{1 - 0.45}{1 - 0.25} \quad (3)$$

Estimates of CBF were obtained From the maximum of the residue Function obtained by deconvolution of the tissue $\Delta R2^*(t)$ curves and arterial input function using singular value decomposition:

$$CBF = \max\{R(t)\} \quad (4)$$

These CBF estimates were cross-calibrated to units of absolute CBF by scaling the mean NAWM CBF value to 22 ml/100 ml/min.

DCE-MRI

Simple algebraic derivations for DCE-NIR,I concentration-time curves without and with correction for confounding T2* recirculation effects can be found in Appendix B. For comparison of the invention method to conventional methods, two versions of $\Delta R1^*(t)$ concentration-time curves were generated and used in the analysis: 1) $\Delta R1(t)$ generated using the first, echo signal of the dual-echo acquisition (equation 54), and 2) $\Delta R1(t)$ generated by extrapolating the first-echo back to TE=O using the dual-echo signals (equation 85). The $\Delta R1(t)$ curves were then converted into tissue concentration-time curves, $C_T(t)$, using equation 37:

$$C_T(t) = [Gd](t) = \frac{\Delta R_1(t)}{\Re_1} \quad (5)$$

where $R_1$ is the longitudinal relaxivity of Gadodiamide at 1.5 T (approximately 4.39 s⁻¹ mM⁻¹ at 37° C.). A surrogate for the plasma concentration-time curve, $C_p(t)$, was determined in a two step process. First, the tissue concentration-time curves for M=3 voxels containing arteries were averaged to determine an arterial concentration-time curve, $C_a(t)$:

$$C_a = \frac{1}{M} \sum_{j=1}^{M} C_{Tj} \quad (6)$$

Second, the arterial concentration-time curve was adjusted for hematocrit to produce the plasma concentration-time curve:

$$C_p(t) = \frac{C_a(t)}{(1 - HCT)} \quad (7)$$

where an assumed value of 0.45 was used for hematocrit (HCT). Pharmacokinetic analysis of DC E-MRI data was then performed using conventional algorithms. Specifically, the volume transfer constant between blood plasma and EES, $K^{trans}$, and the fractional volume of the plasma space, $v_P$, were determined on a voxel-by-voxel basis by linear least squares fitting of the linearized Patlak model to the tissue and plasma concentration-time curves:

$$C_T(t) = K^{trans} \int_0^t C_p(t') dt' + v_P \cdot C_p(t) \quad (8)$$

Results

The methodology and results of correcting DSC-MRI concentration-time curves for confounding recirculation and leakage effects are demonstrated in FIG. 2. FIG. 2a displays the dual-echo time series for the representative tumor voxel depicted on the first and second echo spiral images shown in FIGS. 2b-c. Note that the signals have been truncated to remove the first few points during which the signal approached steady-state. Extravasation of contrast agent is apparent from the increase in signal intensity demonstrated on both the first and second echo signals. By comparing the dual-echo signals, note that leakage of contrast agent begins at the appearance time of the bolus, occurs during the first pass of the bolus, and continues after the first pass of the bolus.

FIG. 2d-f display the $\Delta R2^*(t)$ curve (for the same tumor voxel) obtained from the second-echo signal only (equation 19), along with corresponding rCBV and CBF maps. Note that the curve in 2d is confounded by T1 leakage effects, which causes the post-bolus $\Delta R2^*(t)$ to fall below the pre-bolus baseline and results in an underestimation of rCBV. This effect is apparent by a lack of blood volume in FIG. 2e, which is exacerbated in regions of tumor.

FIGS. 2g-i display the $\Delta R2^*(t)$ curve (for the same tumor voxel) obtained from the ratio of the dual-echo signals (equation 34), along with corresponding rCBV and CBF maps. By using the ratio of the dual-echo signals when constructing $\Delta R2^*(t)$, confounding T1 effects are eliminated, resulting in an increased peak height of $\Delta R2^*(t)$ relative to 2d and the unmasking of the recirculation and T2/T2* leakage effects (evident from the elevated post-bolus baseline). While correction for T1 effects prevents the underestimation of rCRV, an overestimation of rCBV can result from recirculation and any residual susceptibility or dipolar T2 leakage effects.

FIGS. 2j-l display representative $\Delta R2^*(t)$ (red) and $\Delta R2^*(t)$ (blue) curves obtained using equations 35 and 36, along with corresponding rCBV and CBF maps from equation 36. Note that, after this correction, the blue curve shown in FIG. 2j and rCBV and CBF maps in FIGS. 2k-l are no longer confounded by recirculation nor any dipolar T1 and T2 and/or residual susceptibility leakage effects. This results in lower rCBV values seen in FIG. 2k relative to FIG. 2h, most notably in tumor, a result more representative of the true blood volume.

The results of extrapolating the first-echo signal back to TE=0 to correct DCE-MRI concentration-time curves for confounding recirculation and T2/T2* leakage effects is demonstrated in FIG. 3(a-c), the first echo of the dual-echo time series with corresponding $K^{trans}$, and $v_p$, parameter maps; (d-f), the corrected first-echo time series with corresponding $K^{trans}$ and $v_p$ parameter maps; $\Delta R2^*(t)$, tissue concentration-time curves, and nonlinear least squares fits of the Patlak model for the conventional and proposed approaches of estimating $\Delta R1(t)$.

Figure 4A:
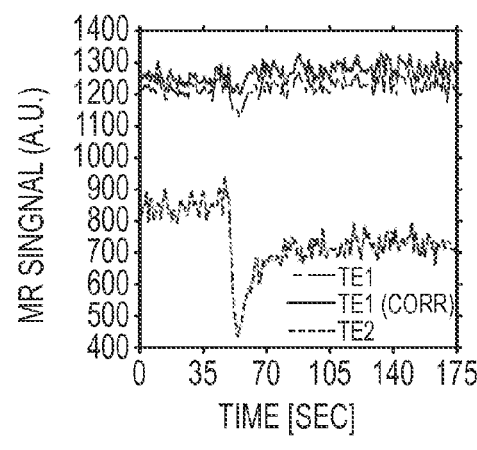
FIGS. 4(a) and (b) illustrate the confounding effects of T2* on signals used to generate DCE-MRI data.
Figure 4B:
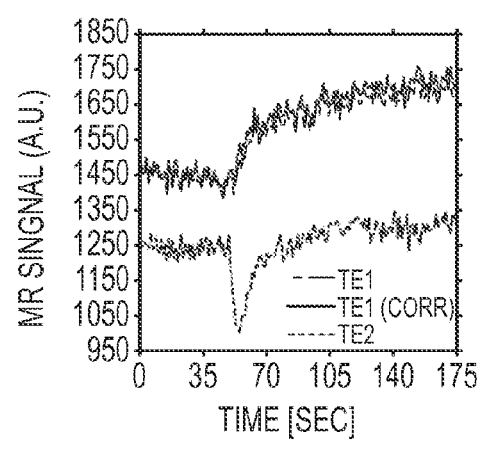

FIG. 4 demonstrates the effect of correcting DCE-MRI time series for T2/T2* effects. FIG. 4a displays the first, corrected first, and second echo signals for a voxel in an artery. A concentrated bolus of gadolinium produces a transient signal decrease in both the first and second echo signals during the first pass. The fact that a transient signal decrease is observed in the first (strongly T1W) signal demonstrates the potentially confounding effects of T2/T2* on DCE-MRI signals, which are recovered in the corrected signal by using the dual echo signals to extrapolate the first echo signal back to TE=0. This suggests that, even though DCE-MRI data is strongly T1-weighted, arterial input functions may be confounded by T2* effects during the first pass of the bolus and should not be neglected. In addition, residual susceptibility effects due to recirculation, evident from the post-bolus portion of the second echo signal remaining below its pre-bolus baseline, are also recovered in the corrected signal. However, it is unlikely that residual susceptibility effects would affect DCE-MRI tissue concentration-time curves due to strong T1 masking effect of the contrast agent. FIG. 4b displays the first, corrected first, and second echo signals for a voxel in tumor. Correction for T2/T2* effects results in a slight increase in the rate of signal enhancement. This suggests that heuristic analysis of DCE-MRI data, based on signal characteristics, could be affected by T2* effects.

Figure 5A:
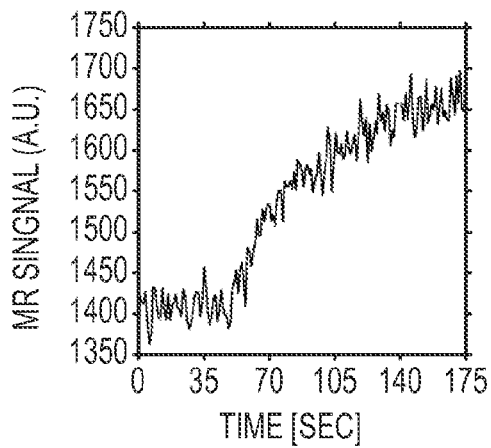
FIGS. 5(a)-(c) illustrate the effects of So estimates on DCE-MRI tissue concentration time curves.
Figure 5B:
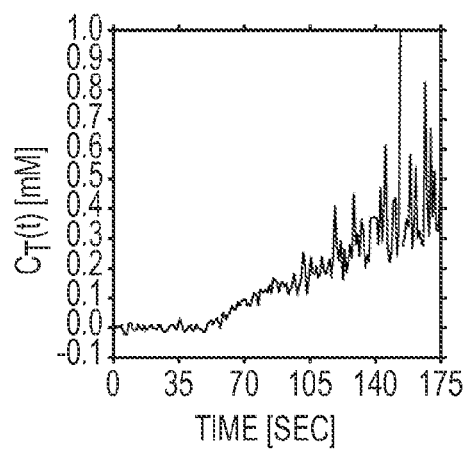
Figure 5C:
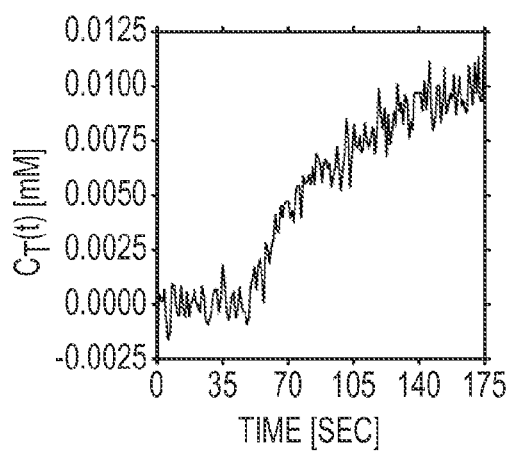
Figure 6A:
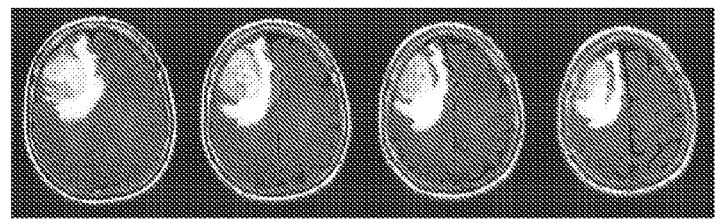
FIG. 6 illustrates various perfusion and permeability parameter maps for a brain tumor.
Figure 6B:
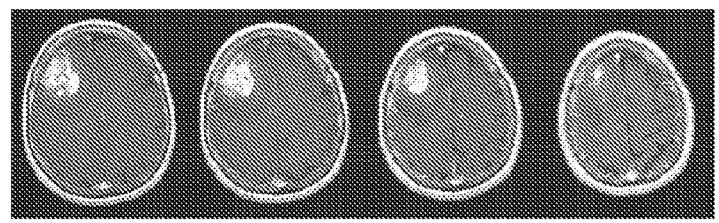
Figure 6C:
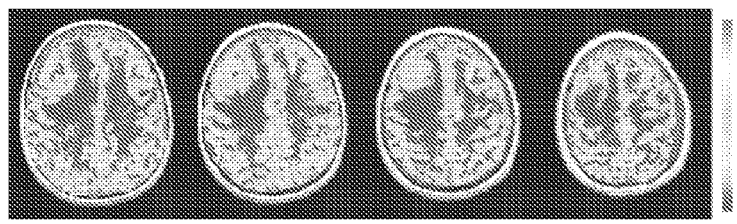
Figure 6D:
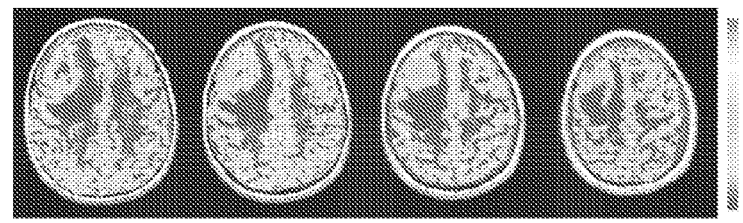
Figure 6E:
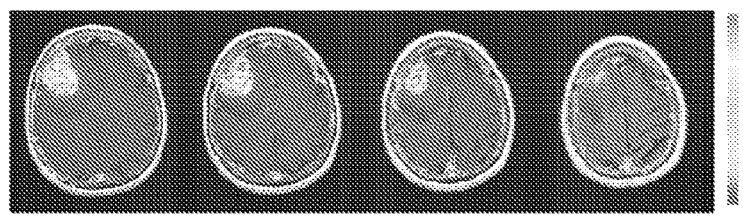
Figure 6F:
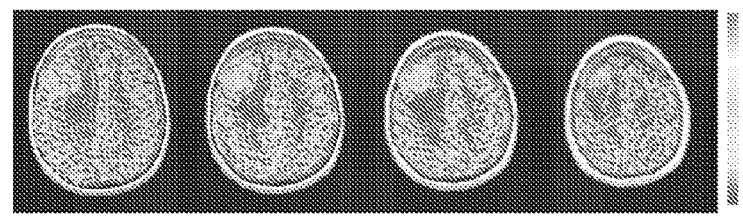

FIG. 5 demonstrates the influence of $S_0$ on DCE-MRI concentration-time curves calculated using equations 54 and 85. Tissue concentration-time curves generated using an underestimated value of $S_0$ exhibit amplified noise when the increased signal intensity approaches the value of $S_0$ (FIG. 5b). This effect can be caused by not waiting long enough for full recovery of longitudinal magnetization between prescan and beginning acquisition. Allowing full recovery of longitudinal magnetization prevents noise amplification and produces a concentration-time curve profile (FIG. 5c) that matches the signal time course (FIG. 5a).

FIG. 6 displays conventional images along with perfusion and permeability parameter maps obtained with the proposed method used for diagnosis of a brain tumor patient: (a) pre-contrast FLAIR, (b) post-contrast T1, (c) rCBV, (d) CBF, (e) $K^{trans}$, (f) $v_p$. Using the method of the present invention, one injection of a standard dose of gadolinium permits calculation of perfusion and permeability parameters corrected for confounding leakage and residual susceptibility effects. Perfusion parameters (i.e., rCBV and CBF) have been corrected for dipolar T1 and T2 leakage and residual susceptibility effects. Permeability parameters (i.e., $K^{trans}$ and $v_p$) have been corrected for dipolar T2 and residual susceptibility effects.

DISCUSSION

The new and novel method of the instant invention permits simultaneous estimation of DSC- and DCE-MRI parameters from a single acquisition using a standard close of contrast agent. Perfusion and permeability parameters are estimated using conventional algorithms and have been corrected for confounding recirculation effects as well as any additional dipolar or residual susceptibility leakage effects. In the context of clinical utility, the disclosed method presents several significant advantages, including:

Reduced total dose of contrast agent. Using the method of the present invention, only a single dose of contrast agent is required to obtain both DSC- and DCE-MRI parameters. Traditionally, estimation of vascularity and vascular permeability required multiple injections of contrast agent. For example, a fairly common approach is to inject a loading dose of contrast agent prior to DSC-MRI acquisition to pre-hance EES tissue thus diminishing confounding T1 leakage effects. In accordance with the present invention, loading doses are no longer required to achieve robust estimates of perfusion parameters in regions of BBB disruptions. Furthermore, minimizing the total dose of contrast agent reduces the risk of developing side effects associated with the contrast agent, including nausea, vomiting, and nephrogenic systemic fibrosis (NSF).

Reduced total acquisition time. This invention facilitates estimation of both DSC- and DCE-MRI parameters in a single acquisition. Traditionally, these parameters were obtained separately using independent acquisitions. Furthermore, separate pre-contrast $S_0$ and T1 calibration scans were required for DCE-MRI analysis. The method herein disclosed provides an alternative approach for estimating $\Delta R1(t)$ curves for DCE-MRI. Rather than using the difference between the dynamic signal and its pre-contrast baseline (as commonly done to eliminate the signal from unsuppressed fat), it estimates $\Delta R1(t)$ directly from the relaxivity equation, requiring only an estimate of $S_0$. Using this approach, a pre-contrast T1 map is not required. In addition, $S_0$ can be estimated internally using the first time point of the single-shot, dual-echo acquisition. By reducing total scan time, increased patient throughput can be achieved.

Improved accuracy of perfusion and permeability estimates while maintaining good, normal brain-to tumor contrast T1 and T2 leakage and residual susceptibility effects confound DSC-MRI parameters. Dual-echo acquisitions allows for estimation of T2* effects directly from the signal equations, which can then be used to extrapolate the DCE signal back to TE=0, thus eliminating the influence of T2 or T2* effects on the dynamic time series. Note that the novel methodology permits both heuristic and pharmacokinetic analysis of DCE-MRI data. Moreover, by correcting for recirculation effects, the accuracy of both DCE approaches should be improved. By correcting for recirculation, errors in the AIF for DCE should be improved. The shorter TR achieved improves temporal resolution, corresponding to better sampling for ATF selection.

DSC and DCE-MRI parameters can be estimated using conventional algorithms. In accordance with the present invention, exotic models are not required to estimate DSC- and DCE-MRI parameters simultaneously. Although the Patlak model was used for pharmacokinetic analysis, other DCE-MRI models could be readily applied.

The spiral-based dual-echo approach described herein offers some important advantages for perfusion imaging. While previous methods for simultaneously acquiring dual echo time courses have relied on keyhole acquisitions or segmented echo-planar imaging, spiral reduces readout times by eliminating the filling of unused data in the corners of k-space and, consequently, permits an increased slice number, increased resolution, or shorter TR capabilities. The shorter readout duration reduces resolution loss due to T2* decay, which diminishes vessel blooming. Specific to DCE-MRI, because the readout starts in the center of k-space, spirals can achieve very short minimum echo times, producing images with good T1 weighting. Second, by starting at the center of k-space, spiral is gradient moment compensated to all orders, which diminishes flow displacement artifacts.

The major disadvantage of spiral is off-resonance induced blurring, which is exacerbated by the time duration of the spiral readout. Off-resonance effects arise from chemical shift differences (i.e., fat and water resonant frequency difference), field inhomogeneity effects, and local static susceptibility differences. Selective excitation of water using spatial-spectral excitation pulses reduces the chemical shift influence of blurring. Reduction of field inhomogeneity effects is accomplished by good shimming and application of off resonance correction algorithms. Several of these algorithms require estimation of field map which can be easily incorporated into the dual-echo acquisition. Incorporation of parallel imaging (e.g., spiral SENSE) would provide substantial benefits for the single-shot dual-echo spiral acquisition herein described. Parallel imaging would facilitate the ability to acquire higher increased number of slices within a given TR or additional echoes. Most importantly, by reducing the length of the spiral readout with parallel imaging, off resonance and susceptibility effects would be reduced. This would greatly improve data, quality in regions of static susceptibility differences, such as resection cavities.

Although the present invention does not require estimation of a precontrast T1 map, there is a dependence on the signal-to-noise ratio and number of precontrast baseline points sampled in the DCE acquisition. Poor signal-to-noise ratio and a small number of pre-contrast baseline points could affect the accuracy of the baseline signal estimate, and thus, initial T1 estimate. However, errors associated with determining precontrast T1 from a separate calibration scan could also propogate into estimation of $\Delta R1$. A flip angle of 72 degrees (the Ernst angle) was used in an embodiment to maximize signal-to-noise ratio, and 60 baseline points were acquired. Both of these factors were selected to improve the accuracy of the precontrast baseline signal intensity.

The method of the instant invention that allows simultaneous estimation of DSC- and DCE-MRI in one acquisition, using a, single dose of contrast agent. Conventional algorithms are used to obtain the perfusion and permeability parameters corrected for recirculation and leakage effects. This method does not require administration of a loading dose of contrast agent, and pre-contrast spin density and native T1 calibration scans (traditionally required for DOE) have been eliminated, resulting in a superior technique performing DSC- and DCE-MRI studies in brain tumors.

APPENDIX A

A.1 Conventional DSC-MRI

The concentration-time curves in DSC-MRI are generated based on an assumed linear relationship between gadolinium concentration and the change in apparent transverse relaxation rate induced by first passage of the contrast agent through the vasculature:

$$\Delta R_2^*(t) = \frac{1}{T_2^*(t)} - \frac{1}{T_{2_0}^*} = \kappa [Gd](t) \quad (9)$$

where k is a constant dependent on transverse relaxivity, field strength, pulse sequence, and vascular morphology. In conventional DSC-MRI, a rapid acquisition method is used to acquire susceptibility-weighted images and the pulse sequences typically employed are of the spoiled gradient-echo family (i.e., echo-planar, spiral. FLASH, etc.). The generalized signal equation for conventional DSC-MRI is then:

$$S(t) = S_0 \sin\theta \left[ \frac{1 - e^{\frac{-TR}{T_1(t)}}}{1 - \cos\theta e^{\frac{-TR}{T_1(t)}}} \right] e^{\frac{-TE}{T_2^*(t)}} \quad (10)$$

where T1(t) and T2*(t), indicate that these parameters can change dynamically during acquisition. Solving equation 10 for 1/T2* (t) yields:

$$\frac{1}{T_2^*(t)} = \frac{-1}{TE} \ln \left( \frac{S(t)}{S_0 \sin\theta \left[ \frac{1 - e^{\frac{-TR}{T_1(t)}}}{1 - \cos\theta e^{\frac{-TR}{T_1(t)}}} \right]} \right) \quad (11)$$

In order to determine the change in apparent transverse relaxation rate (i.e., $\Delta R2^*(t)$) an estimate of the pre-contrast apparent transverse relaxation rate (i.e., $T2_0^*$) must be obtained. This is achieved in two steps. First, the pre-contrast baseline signal. $S_B$, is determined by averaging S(t) over the first $N_B$ baseline points:

$$S_B = \frac{1}{N_B} \sum_{i=1}^{N_B} \left( S_0 \sin\theta \left[ \frac{1 - e^{\frac{-TR}{T_{1_0}}}}{1 - \cos\theta e^{\frac{-TR}{T_{1_0}}}} \right] e^{\frac{-TE}{T_{2_0}^*}} \right)_i \quad (12)$$

Note that because the contrast agent has not yet been administered, constant initial values of $T1_0$ and $T2_0$ are used in the expression. Second, the result of equation 12 is solved for $1/T2_0^*$, which yields:

$$\frac{1}{T^*_{2_0}} = \frac{-1}{TE} \ln\left(\frac{S_B}{S_0 \sin\theta \left[\frac{1-e^{\frac{-TR}{T_{1_0}}}}{1-\cos\theta e^{\frac{-TR}{T_{1_0}}}}\right]}\right) \quad (13)$$

Substituting the results of equations 11 and 13 into equation 9:

$$\Delta R^*_2(t) = \frac{-1}{TE} \ln\left(\frac{S(t)}{S_0 \sin\theta \left[\frac{1-e^{\frac{-TR}{T_1(t)}}}{1-\cos\theta e^{\frac{-TR}{T_1(t)}}}\right]}\right) - \frac{-1}{TE} \ln\left(\frac{S_B}{S_0 \sin\theta \left[\frac{1-e^{\frac{-TR}{T_{1_0}}}}{1-\cos\theta e^{\frac{-TR}{T_{1_0}}}}\right]}\right) \quad (14)$$

$$= \frac{-1}{TE}\left[\ln\left(\frac{S(t)}{S_0 \sin\theta \left[\frac{1-e^{\frac{-TR}{T_1(t)}}}{1-\cos\theta e^{\frac{-TR}{T_1(t)}}}\right]}\right) - \ln\left(\frac{S_B}{S_0 \sin\theta \left[\frac{1-e^{\frac{-TR}{T_{1_0}}}}{1-\cos\theta e^{\frac{-TR}{T_{1_0}}}}\right]}\right)\right] \quad (15)$$

$$= \frac{-1}{TE} \ln\left(\frac{\frac{S(t)}{S_0 \sin\theta \left[\frac{1-e^{\frac{-TR}{T_1(t)}}}{1-\cos\theta e^{\frac{-TR}{T_1(t)}}}\right]}}{\frac{S_B}{S_0 \sin\theta \left[\frac{1-e^{\frac{-TR}{T_{1_0}}}}{1-\cos\theta e^{\frac{-TR}{T_{1_0}}}}\right]}}\right) \quad (16)$$

$$= \frac{-1}{TE} \ln\left(\frac{S(t)}{S_0 \sin\theta \left[\frac{1-e^{\frac{-TR}{T_1(t)}}}{1-\cos\theta e^{\frac{-TR}{T_1(t)}}}\right]} \cdot \frac{S_0 \sin\theta \left[\frac{1-e^{\frac{-TR}{T_{1_0}}}}{1-\cos\theta e^{\frac{-TR}{T_{1_0}}}}\right]}{S_B}\right) \quad (17)$$

$$\Delta R^*_2(t) = \frac{-1}{TE} \ln\left(\frac{S(t)}{\left[\frac{1-e^{\frac{-TR}{T_1(t)}}}{1-\cos\theta e^{\frac{-TR}{T_1(t)}}}\right]} \cdot \frac{\left[\frac{1-e^{\frac{-TR}{T_{1_0}}}}{1-\cos\theta e^{\frac{-TR}{T_{1_0}}}}\right]}{S_B}\right) \quad (18)$$

Equation 18 demonstrates the potential influence of dipolar T1 effects on concentration-time curves obtained with DSC-MRI. In the presence of an intact BBB, the contrast agent remains confined to the vasculature (i.e., no extravasation occurs). T1(t) is reduced to $T1_0^*$ (i.e., its pre-contrast value), and $\Delta R2^*(t)$ reduces to its usual form:

$$\Delta R^*_2(t) = \frac{-1}{TE} \ln\left(\frac{S(t)}{S_B}\right) \quad (19)$$

A.2 Correcting DSC-MRI Time Courses for Extravasation Effects

Dual-echo acquisition methods provide an effective means by which confounding dipolar T1 leakage effects can be eliminated from DSC-MRI time courses. The signal equations for the first and second echoes are:

$$S_{TE_1}(t) = S_0 \sin\theta \left[\frac{1-e^{\frac{-TR}{T_1(t)}}}{1-\cos\theta e^{\frac{-TR}{T_1(t)}}}\right] e^{\frac{-TE_1}{T^*_2(t)}} \quad (20)$$

$$S_{TE_2}(t) = S_0 \sin\theta \left[\frac{1-e^{\frac{-TR}{T_1(t)}}}{1-\cos\theta e^{\frac{-TR}{T_1(t)}}}\right] e^{\frac{-TE_2}{T^*_2(t)}} \quad (21)$$

Solving for $1/T2^*(t)$ using the ration of the two signal equations yields:

$$\frac{S_{TE_1}(t)}{S_{TE_2}(t)} = \frac{S_0 \sin\theta \left[\frac{1-e^{\frac{-TR}{T_1(t)}}}{1-\cos\theta e^{\frac{-TR}{T_1(t)}}}\right] e^{\frac{-TE_1}{T^*_2(t)}}}{S_0 \sin\theta \left[\frac{1-e^{\frac{-TR}{T_1(t)}}}{1-\cos\theta e^{\frac{-TR}{T_1(t)}}}\right] e^{\frac{-TE_2}{T^*_2(t)}}} \quad (22)$$

$$= \frac{e^{\frac{-TE_1}{T^*_2(t)}}}{e^{\frac{-TE_2}{T^*_2(t)}}} \quad (23)$$

$$= e^{\frac{+TE_2}{T^*_2(t)}} e^{\frac{-TE_1}{T^*_2(t)}} \quad (24)$$

$$= e^{\frac{(TE_2-TE_1)}{T^*_2(t)}} \quad (25)$$

$$\ln\left(\frac{S_{TE_1}(t)}{S_{TE_2}(t)}\right) = \frac{(TE_2-TE_1)}{T^*_2(t)} \quad (26)$$

$$\frac{1}{T^*_2(t)} = \frac{1}{(TE_2-TE_1)} \ln\left(\frac{S_{TE_1}(t)}{S_{TE_2}(t)}\right) \quad (27)$$

Again, the pre-contrast apparent transverse relaxation rate (i.e., $1/T2_0^*$) must be estimated in order to determine the change in apparent transverse relaxation rate. The first step is to average the signals over the first $N_B$ baseline points:

$$S_{TE_{1_B}} = \frac{1}{N_B} \sum_{i=1}^{N_B} \left(S_0 \sin\theta \left[\frac{1-e^{\frac{-TR}{T_{1_0}}}}{1-\cos\theta e^{\frac{-TR}{T_{1_0}}}}\right] e^{\frac{-TE_1}{T^*_{2_0}}}\right)_i \quad (28)$$

$$S_{TE_{2_B}} = \frac{1}{N_B} \sum_{i=1}^{N_B} \left(S_0 \sin\theta \left[\frac{1-e^{\frac{-TR}{T_{1_0}}}}{1-\cos\theta e^{\frac{-TR}{T_{1_0}}}}\right] e^{\frac{-TE_2}{T^*_{2_0}}}\right)_i \quad (29)$$

Because contrast agent has not yet been administered, constant initial values of $T1_0^*$ and $T2_0^*$ are used in the expressions. Solving for $1/T2_0^*$ using the ratio of the baseline signals yields:

$$\frac{1}{T_{2_0}^*} = \frac{1}{(TE_2 - TE_1)} \ln\left(\frac{S_{TE_{1_B}}}{S_{TE_{2_B}}}\right) \quad (30)$$

Substituting the results of equations 27 and 30 into equation 9, the following relationship is obtained:

$$\Delta R_2^*(t) = \frac{1}{(TE_2 - TE_1)} \ln\left(\frac{S_{TE_1}(t)}{S_{TE_2}(t)}\right) - \frac{1}{(TE_2 - TE_1)} \ln\left(\frac{S_{TE_{1_B}}}{S_{TE_{2_B}}}\right) \quad (31)$$

$$= \frac{1}{(TE_2 - TE_1)} \left[\ln\left(\frac{S_{TE_1}(t)}{S_{TE_2}(t)}\right) - \ln\left(\frac{S_{TE_{1_B}}}{S_{TE_{2_B}}}\right)\right] \quad (32)$$

$$= \frac{1}{(TE_2 - TE_1)} \ln\left(\frac{\frac{S_{TE_1}(t)}{S_{TE_2}(t)}}{\frac{S_{TE_{1_B}}}{S_{TE_{2_B}}}}\right) \quad (33)$$

$$\Delta R_2^*(t) = \frac{1}{(TE_2 - TE_1)} \ln\left(\frac{S_{TE_1}(t)}{S_{TE_2}(t)} \frac{S_{TE_{2_B}}}{S_{TE_{1_B}}}\right) \quad (34)$$

Equation 34 is the DSC-MRI concentration-time curve free from dipolar T1 leakage effects. In practice, another potential confounding effect on DSC concentration-time curves characterized as elevated endlines that develop after the first pass of contrast agent has been observed. The effect seems to be exacerbated in tumors relative to normal brain, which implies that there could be a susceptibility or T2 leakage effect in these regions in addition to recirculation. The source of the elevated endlines could therefore be due to dipolar T2 effects, residual susceptibility effects from the contrast agent, or some combination of both. Correction for these effects is performed by non-linear least squares fitting of a model to the corrupted $\Delta R2^*(t)$ concentration-time curves that accounts for both the first pass and recirculation:

$$\Delta R_2^*(t)' = k(t - t_0)^\alpha e^{-\frac{(t-t_0)}{\beta}} + h \int_0^t k(t' - t_0)^\alpha e^{-\frac{(t'-t_0)}{\beta}} dt' \quad (35)$$

where k is a scale factor, $t_0$ is the appearance time of the bolus, $\alpha$, and $\beta$ are fit parameters of a gamma-variate and h is used to scale the cumulative integral of the gamma-variate. After non-linear least squares fitting, $\Delta R2^*(t)$ curves corrected for dipolar T1 and T2 and residual susceptibility effects are generated by constructing gamma-variates using the parameters estimated from the full model fit:

$$\Delta R_2^*(t) = k(t - t_0)^\alpha e^{-\frac{(t-t_0)}{\beta}} \quad (36)$$

Conventional algorithms can then be applied to generate estimates of DSC-MRI parameters free from confounding contrast agent effects using equation 36.

B. APPENDIX B

B.1 Conventional DCE-MRI

The concentration-time curves in DCE-MRI are generated based on an assumed linear relationship between gadolinium concentration and the change in spin-lattice relaxation rate induced by extravasation of the contrast agent from the vasculature to the extracellular, extravascular space, where dipolar interaction between the unpaired electrons of the contrast agent and local tissue protons ensues:

$$\Delta R_1(t) = \frac{1}{T_1(t)} - \frac{1}{T_{1_o}} = \Re_1 [Gd](t) \quad (37)$$

The DCE-MRI technique relies on the sensitivity of the pulse sequence to changes in signal intensity caused by T1 shortening. Traditionally, conventional 2D or 3D spoiled gradient echo sequences are often used in DCE-MRI because they provide good image quality with sufficient temporal resolution. Analogous to DSC-MRI, the generalized signal equation for DCE-MRI is then equivalent to that in equation 10.

Several methods have been used in the literature to convert the dynamic signal intensity time courses into tissue gadolinium concentration-time curves. In the method used here (which is similar to the Hittmair approach). $1/T1(t)$ and $1/T1_o$ are obtained directly by solving the pre- and post-contrast signal equations and the results, along with equation 37, are used to determine the $\Delta R1(t)$. To begin, equation 10 is solved for $1/T1(t)$:

$$S(t) = S_0 \sin\theta \left[\frac{1 - e^{\frac{-TR}{T_1(t)}}}{1 - \cos\theta e^{\frac{-TR}{T_1(t)}}}\right] e^{\frac{-TE}{T_2^*(t)}} \quad (38)$$

$$\frac{S(t)}{S_0 \sin\theta e^{\frac{-TE}{T_2^*(t)}}} = \frac{1 - e^{\frac{-TR}{T_1(t)}}}{1 - \cos\theta e^{\frac{-TR}{T_1(t)}}} \quad (39)$$

$$\left(1 - \cos\theta e^{\frac{-TR}{T_1(t)}}\right)\left[\frac{S(t)}{S_0 \sin\theta e^{\frac{-TE}{T_2^*(t)}}}\right] = 1 - e^{\frac{-TR}{T_1(t)}} \quad (40)$$

$$\frac{S(t)}{S_0 \sin\theta e^{\frac{-TE}{T_2^*(t)}}} - \frac{S(t)\cos\theta e^{\frac{-TR}{T_1(t)}}}{S_0 \sin\theta e^{\frac{-TE}{T_2^*(t)}}} = 1 - e^{\frac{-TR}{T_1(t)}} \quad (41)$$

$$e^{\frac{-TR}{T_1(t)}} - \frac{S(t)\cos\theta e^{\frac{-TR}{T_1(t)}}}{S_0 \sin\theta e^{\frac{-TE}{T_2^*(t)}}} = 1 - \frac{S(t)}{S_0 \sin\theta e^{\frac{-TE}{T_2^*(t)}}} \quad (42)$$

$$e^{\frac{-TR}{T_1(t)}}\left[1 - \frac{S(t)\cos\theta}{S_0 \sin\theta e^{\frac{-TE}{T_2^*(t)}}}\right] = 1 - \frac{S(t)}{S_0 \sin\theta e^{\frac{-TE}{T_2^*(t)}}} \quad (43)$$

$$e^{\frac{-TR}{T_1(t)}}\left[S_0 \sin\theta e^{\frac{-TE}{T_2^*(t)}} - S(t)\cos\theta\right] = S_0 \sin\theta e^{\frac{-TE}{T_2^*(t)}} - S(t) \quad (44)$$

$$e^{\frac{-TR}{T_1(t)}} = \frac{S_0 \sin\theta e^{\frac{-TE}{T_2^*(t)}} - S(t)}{S_0 \sin\theta e^{\frac{-TE}{T_2^*(t)}} - S(t)\cos\theta} \quad (45)$$

$$\frac{-TR}{T_1(t)} = \ln\left[\frac{S_0 \sin\theta e^{\frac{-TE}{T_2^*(t)}} - S(t)}{S_0 \sin\theta e^{\frac{-TE}{T_2^*(t)}} - S(t)\cos\theta}\right] \quad (46)$$

$$\frac{1}{T_1(t)} = \frac{-1}{TR}\ln\left[\frac{S_0\sin\theta e^{\frac{-TE}{T_2^*(t)}} - S(t)}{S_0\sin\theta e^{\frac{-TE}{T_2^*(t)}} - S(t)\cos\theta}\right] \quad (47)$$

In order to determine the change in spin lattice relaxation rate (i.e., $\Delta R1(t)$), an estimate of the pre-contrast spin lattice relaxation rate (i.e., $T1_0$) must be obtained. This is achieved in two steps. First, the pre-contrast baseline signal, $S_B$, is determined by averaging $S(t)$ over the first $N_B$ baseline points:

$$S_B = \frac{1}{N_B}\sum_{i=1}^{N_B}\left(S_0\sin\theta\left[\frac{1-e^{\frac{-TR}{T1_0}}}{1-\cos\theta e^{\frac{-TR}{T1_0}}}\right]e^{\frac{-TE}{T_{2_0}^*}}\right)_i \quad (48)$$

Note that because the contrast agent has not yet been administered, constant initial values of $T1_0$ and $1/T1_0$ are used in the expression. Second, the result of equation 48 is then solved for $1/T1_0$, which yields:

$$\frac{1}{T1_0} = \frac{-1}{TR}\ln\left[\frac{S_0\sin\theta e^{\frac{-TE}{T_{2_0}^*}} - S_B}{S_0\sin\theta e^{\frac{-TE}{T_{2_0}^*}} - S_B\cos\theta}\right] \quad (49)$$

Substituting equations 47 and 49 into equation 37:

$$\Delta R_1(t) = \frac{-1}{TR}\ln\left[\frac{S_0\sin\theta e^{\frac{-TE}{T_2^*(t)}} - S(t)}{S_0\sin\theta e^{\frac{-TE}{T_2^*(t)}} - S(t)\cos\theta}\right] - \frac{-1}{TR}\ln\left[\frac{S_0\sin\theta e^{\frac{-TE}{T_{2_0}^*}} - S_B}{S_0\sin\theta e^{\frac{-TE}{T_{2_0}^*}} - S_B\cos\theta}\right] \quad (50)$$

$$= \frac{-1}{TR}\left[\ln\left[\frac{S_0\sin\theta e^{\frac{-TE}{T_2^*(t)}} - S(t)}{S_0\sin\theta e^{\frac{-TE}{T_2^*(t)}} - S(t)\cos\theta}\right] - \ln\left[\frac{S_0\sin\theta e^{\frac{-TE}{T_{2_0}^*}} - S_B}{S_0\sin\theta e^{\frac{-TE}{T_{2_0}^*}} - S_B\cos\theta}\right]\right] \quad (51)$$

$$= \frac{-1}{TR}\ln\left[\frac{\left[\frac{S_0\sin\theta e^{\frac{-TE}{T_2^*(t)}} - S(t)}{S_0\sin\theta e^{\frac{-TE}{T_2^*(t)}} - S(t)\cos\theta}\right]}{\left[\frac{S_0\sin\theta e^{\frac{-TE}{T_{2_0}^*}} - S_B}{S_0\sin\theta e^{\frac{-TE}{T_{2_0}^*}} - S_B\cos\theta}\right]}\right] \quad (52)$$

$$\Delta R_1(t) = \frac{-1}{TR}\ln\left[\frac{\left[\frac{S_0\sin\theta e^{\frac{-TE}{T_2^*(t)}} - S(t)}{S_0\sin\theta e^{\frac{-TE}{T_2^*(t)}} - S(t)\cos\theta}\right]}{\left[\frac{S_0\sin\theta e^{\frac{-TE}{T_{2_0}^*}} - S_B\cos\theta}{S_0\sin\theta e^{\frac{-TE}{T_{2_0}^*}} - S_B}\right]}\right] \quad (53)$$

Equation 53 demonstrates the potential influence of T2* effects on concentration-time curves obtained with DCE-MRI. Since minimum echo times are used in DCE-MRI to obtain good T1 weighting, it is widely assumed that insignificant phase dispersion will occur over time scales of short TE (i.e., TE<<T2*). Consequently, T2* effects are generally ignored, which results in the following approximation:

$$\Delta R_1(t) \approx \frac{-1}{TR}\ln\left[\left[\frac{S_0\sin\theta - S(t)}{S_0\sin\theta - S(t)\cos\theta}\right]\left[\frac{S_0\sin\theta - S_B\cos\theta}{S_0\sin\theta - S_B}\right]\right] \quad (54)$$

Equation 54 does not exhibit a dependence on the initial pre-contrast spin lattice relaxation time (i.e., $T1_0$), which eliminates the requirement of having to acquire a separate pre-contrast calibration scan. Instead, $T1_0$ is determined directly from the pre-contrast baseline signal intensity. In addition, notice that $\Delta R1(t)$ can be estimated directly from $S(t)$, provided that an estimate of $S_0$ be obtained.

Assuming fully relaxed spins, $S_0$ can be estimated from a single-shot, single repetition (i.e., infinite TR), dual-echo scan. In the limit that TR→∞ (which is valid for a single repetition), the signal equations for the first and second echoes (i.e. equations 20 and 21) reduce to:

$$S_{TE_{1_0}} = S_0\sin\theta e^{\frac{-TE_1}{T_{2_0}^*}} \quad (55)$$

$$S_{TE_{2_0}} = S_0\sin\theta e^{\frac{-TE_2}{T_{2_0}^*}} \quad (56)$$

Using the same methodology that was used to generate equation 30, $1/T2_0^{**}$ is estimated as:

$$\frac{1}{T_{2_0}^*} = \frac{1}{(TE_2 - TE_1)}\ln\left(\frac{S_{TE_{1_0}}}{S_{TE_{2_0}}}\right) \quad (57)$$

Substituting equation 57 into equation 55 and rearranging. $S_0$ is estimated as:

$$S_{TE_{1_0}} = S_0\sin\theta e^{\frac{-TE_1}{T_{2_0}^*}} \quad (58)$$

$$= S_0\sin\theta e^{\frac{-TE_1}{TE_2-TE_1}\ln\left(\frac{S_{TE_{1_0}}}{S_{TE_{2_0}}}\right)} \quad (59)$$

$$\frac{S_{TE_{1_0}}}{S_0\sin\theta} = e^{\frac{-TE_1}{TE_2-TE_1}\ln\left(\frac{S_{TE_{1_0}}}{S_{TE_{2_0}}}\right)} \quad (60)$$

$$\ln\left(\frac{S_{TE_{1_0}}}{S_0\sin\theta}\right) = \frac{-TE_1}{TE_2-TE_1}\ln\left(\frac{S_{TE_{1_0}}}{S_{TE_{2_0}}}\right) \quad (61)$$

$$-\ln\left(\frac{S_0\sin\theta}{S_{TE_{1_0}}}\right) = \frac{-TE_1}{TE_2-TE_1}\ln\left(\frac{S_{TE_{1_0}}}{S_{TE_{2_0}}}\right) \quad (62)$$

$$\ln\left(\frac{S_0\sin\theta}{S_{TE_{1_0}}}\right) = \frac{TE_1}{TE_2-TE_1}\ln\left(\frac{S_{TE_{1_0}}}{S_{TE_{2_0}}}\right) \quad (63)$$

$$\frac{S_0\sin\theta}{S_{TE_{1_0}}} = e^{\frac{TE_1}{TE_2-TE_1}\ln\left(\frac{S_{TE_{1_0}}}{S_{TE_{2_0}}}\right)} \quad (64)$$

$$S_0 = \frac{S_{TE_{1_0}}}{\sin\theta} e^{\frac{TE_1}{TE_2 - TE_1} \ln\left[\frac{S_{TE_{1_0}}}{S_{TE_{2_0}}}\right]} \quad (65)$$

Note that if a 90 degree flip angle is used the sine term in the denominator vanishes. The estimate of $S_0$ is then substituted into equation 54 to yield the change in spin lattice relaxation rate, which is then used to determine the concentration-time curves using equation 37.

B.2 Correcting DCE Time Courses for T2/T2* Effects

Dual-echo acquisitions offer two significant advantages for DCE-MRI. One advantage is that, assuming spins had fully relaxed prior to beginning the scan, $S_0$ can be determined from the first time point (i.e. first repetition) of a single-shot. dual-echo acquisition using the methodology described in equations 55-65. This factor results in a significant time savings in that no additional pre-contrast calibration scans are required to convert the DCE-MRI signal time courses into concentration-time curves.

The second advantage of dual-echo acquisitions is that confounding T2* effects can be eliminated from the DCE concentration-time curves. This is performed in a two-step process. First, $1/T2^*(t)$ is estimated at each time point from the first and second echo signal equations (i.e., equations 20 and 21) using the same methodology to that used to generate equation 27. Second, a corrected first echo signal, $S_{TE1c}(t)$ is obtained by extrapolating each time point of the first echo signal in equation 20 back to TE=O using:

$$S_{TE_{1_C}}(t) = S_{TE_1}(t) e^{\frac{+TE_1}{T_2^*(t)}} \quad (66)$$

Substituting equations 20 and 27 into equation 66:

$$S_{TE_{1_C}}(t) = \left[S_0 \sin\theta \left[\frac{1 - e^{\frac{-TR}{T_1(t)}}}{1 - \cos\theta e^{\frac{-TR}{T_1(t)}}}\right] e^{\frac{-TE_1}{T_2^*(t)}}\right] e^{\frac{+TE_1}{T_2^*(t)}} \quad (67)$$

$$= \left[\frac{S_0 \sin\theta \left[\frac{1 - e^{\frac{-TR}{T_1(t)}}}{1 - \cos\theta e^{\frac{-TR}{T_1(t)}}}\right]}{e^{\frac{-TE_1}{TE_2 - TE_1} \ln\left[\frac{S_{TE_1}(t)}{S_{TE_2}(t)}\right]}}\right] e^{\frac{+TE_1}{TE_2 - TE_1} \ln\left[\frac{S_{TE_1}(t)}{S_{TE_2}(t)}\right]} \quad (68)$$

$$S_{TE_{1_C}}(t) = S_0 \sin\theta \left[\frac{1 - e^{\frac{-TR}{T_1(t)}}}{1 - \cos\theta e^{\frac{-TR}{T_1(t)}}}\right] \quad (69)$$

Notice that T2* effects have been eliminated in the corrected signal equation. Solving equation 69 for $1/T1(t)$ yields:

$$S_{TE_{1_C}}(t) = S_0 \sin\theta \left[\frac{1 - e^{\frac{-TR}{T_1(t)}}}{1 - \cos\theta e^{\frac{-TR}{T_1(t)}}}\right] \quad (70)$$

$$\frac{S_{TE_{1_C}}(t)}{S_0 \sin\theta} = \frac{1 - e^{\frac{-TR}{T_1(t)}}}{1 - \cos\theta e^{\frac{-TR}{T_1(t)}}} \quad (71)$$

$$\left(1 - \cos\theta e^{\frac{-TR}{T_1(t)}}\right)\left[\frac{S_{TE_{1_C}}(t)}{S_0 \sin\theta}\right] = 1 - e^{\frac{-TR}{T_1(t)}} \quad (72)$$

$$\frac{S_{TE_{1_C}}(t)}{S_0 \sin\theta} - \frac{S_{TE_{1_C}}(t) \cos\theta e^{\frac{-TR}{T_1(t)}}}{S_0 \sin\theta} = 1 - e^{\frac{-TR}{T_1(t)}} \quad (73)$$

$$e^{\frac{-TR}{T_1(t)}} - \frac{S_{TE_{1_C}}(t) \cos\theta e^{\frac{-TR}{T_1(t)}}}{S_0 \sin\theta} = 1 - \frac{S_{TE_{1_C}}(t)}{S_0 \sin\theta} \quad (74)$$

$$e^{\frac{-TR}{T_1(t)}}\left[1 - \frac{S_{TE_{1_C}}(t) \cos\theta}{S_0 \sin\theta}\right] = 1 - \frac{S_{TE_{1_C}}(t)}{S_0 \sin\theta} \quad (75)$$

$$e^{\frac{-TR}{T_1(t)}}\left[S_0 \sin\theta - S_{TE_{1_C}}(t) \cos\theta\right] = S_0 \sin\theta - S_{TE_{1_C}}(t) \quad (76)$$

$$e^{\frac{-TR}{T_1(t)}} = \frac{S_0 \sin\theta - S_{TE_{1_C}}(t)}{S_0 \sin\theta - S_{TE_{1_C}}(t) \cos\theta} \quad (77)$$

$$\frac{-TR}{T_1(t)} = \ln\left[\frac{S_0 \sin\theta - S_{TE_{1_C}}(t)}{S_0 \sin\theta - S_{TE_{1_C}}(t) \cos\theta}\right] \quad (78)$$

$$\frac{1}{T_1(t)} = \frac{-1}{TR} \ln\left[\frac{S_0 \sin\theta - S_{TE_{1_C}}(t)}{S_0 \sin\theta - S_{TE_{1_C}}(t) \cos\theta}\right] \quad (79)$$

In order to determine the change in spin lattice relaxation rate (i.e., $\Delta R1^*(t)$), an estimate of the pre-contrast spin lattice relaxation rate (i.e., $T1_0$) must be obtained. This is achieved in two steps. First, the corrected pre-contrast baseline signal, $S_{BC}$, is determined by averaging $S_{TE1c}(t)$ over the first $N_B$ baseline points:

$$S_{B_C} = \frac{1}{N_B} \sum_{i=1}^{N_B} \left(S_0 \sin\theta \left[\frac{1 - e^{\frac{-TR}{T_{1_0}}}}{1 - \cos\theta e^{\frac{-TR}{T_{1_0}}}}\right]\right)_i \quad (80)$$

Note that because the contrast agent has not yet been administered, constant initial values of $T1_0$, and $1/T2_0^*$ are used in the expression. Second, equation 80 is then solved for $1/T1_0$, which yields:

$$\frac{1}{T_{1_0}} = \frac{-1}{TR} \ln\left[\frac{S_0 \sin\theta - S_{B_C}}{S_0 \sin\theta - S_{B_C} \cos\theta}\right] \quad (81)$$

Substituting equations 79 and 81 into equation 37:

$$\Delta R_1(t) = \frac{-1}{TR} \ln\left[\frac{S_0 \sin\theta - S_{TE_{1_C}}(t)}{S_0 \sin\theta - S_{TE_{1_C}}(t) \cos\theta}\right] - \frac{-1}{TR} \ln\left[\frac{S_0 \sin\theta - S_{B_C}}{S_0 \sin\theta - S_{B_C} \cos\theta}\right] \quad (82)$$

-continued $$= \frac{-1}{TR} \ln \left[ \left[ \frac{S_0 \sin\theta - \frac{S_{TE_{1_C}}(t)}{S_0 \sin\theta - S_{TE_{1_C}}(t)\cos\theta}} \right] - \ln \left[ \frac{S_0 \sin\theta - S_{B_C}}{S_0 \sin\theta - S_{B_C}\cos\theta} \right] \right] \quad (83)$$

$$= \frac{-1}{TR} \ln \left[ \left[ \frac{\frac{S_0 \sin\theta - S_{TE_{1_C}}(t)}{S_0 \sin\theta - S_{TE_{1_C}}(t)\cos\theta}}{\frac{S_0 \sin\theta - S_{B_C}}{S_0 \sin\theta - S_{B_C}\cos\theta}} \right] \right] \quad (84)$$

$$\Delta R_1(t) = \frac{-1}{TR} \ln \left[ \left[ \frac{S_0 \sin\theta - S_{TE_{1_C}}(t)}{S_0 \sin\theta - S_{TE_{1_C}}(t)\cos\theta} \right] \left[ \frac{S_0 \sin\theta - S_{B_C}\cos\theta}{S_0 \sin\theta - S_{B_C}} \right] \right] \quad (85)$$

Equation 85 is the $\Delta R1(t)$ curve corrected for confounding T2* effects. An estimate of $S_0$, determined from the first time point of the single-shot, dual-echo acquisition, is then substituted into equation 85 to yield the change in spin lattice relaxation rate, which is then used to determine the concentration-time curves using equation 37.

Changes may be made in the above methodology without departing from the scope hereof. It should thus be noted that the matter contained in the above description and/or shown in the accompanying figures should be interpreted as illustrative and not in a limiting sense. The following claims are intended to cover all generic and specific features described herein, as well as all statements of the scope of the present invention which, as a matter of language, might be said to fall therebetween.

What is claimed is:

1. A method for producing an image of an organ or tissue with a magnetic resonance imaging (MRI) system comprising the steps of:
   a) injecting a contrast agent into a blood vessel which induces a differential between the susceptibilities of the blood vessel and a tissue of interest;
   b) utilizing an image processor to acquire MRI image data sets during a first passage of the contrast agent through the tissue of interest using an imaging sequence adapted to collect image data at both short and long echo times (TE);
   c) utilizing a processor to compute image maps of relative cerebral blood volume (rCBV) from data in the acquired MRI image data sets;
   d) correcting the rCBV image maps for variations to T1, T2 and T2* relaxation rates caused by contrast agent extravasation or recirculation;
   e) utilizing a processor to compute image maps of absolute cerebral blood volume (CBV), cerebral blood flow (CBF) and mean transit time (MTT) from data in the acquired image data sets;
   f) correcting the CBV, CBF and MTT image maps for variations to T1, T2 and T2* relaxation rates caused by contrast agent extravasation or recirculation;
   g) utilizing a processor to create T1-weighted DCE parameter maps for preselected DCE permeability parameters from the short echo time (TE) data; and
   h) based on the T1-weighted DCE parameter maps, utilizing a processor to compute perfusion and permeability parameter maps correcting for contrast leakage, and displaying corrected perfusion and permeability maps.

2. The method of claim 1 wherein the preselected permeability parameters of step g) include $K^{trans}$, $v_e$ and $v_p$.

3. The method of claim 1 wherein step c) is performed by:
   a) computing the T2* relaxation rate at each time point $1/R2^*(t)$ from the image data signals collected at the short and long echo times;
   b) fitting a model to the $1/R2^*(t)$ data to account for confounding modifications to T2 or T2*; and
   c) correcting the $1/R2^*$ data for residual T2 or T2* effects.

4. The method of claim 1 wherein step d) is performed by:
   a) computing the T2* relaxation rate at each time point $1/R2^*(t)$ from the image data signals collected at the short and long echo times;
   b) fitting a model to the $1/R2^*(t)$ data to account for confounding modifications to T2 or T2*; and
   c) selecting an arterial input function (AIF) from the $1/R2^*(t)$ data.

5. The method of claim 1 wherein step e) is performed by:
   a) computing the T2* relaxation rate at each time point $1/R2^*(t)$ from the image data signals collected at the short and long echo times;
   b) correcting the short echo time image data signals for T2 or T2* effects using the data signals collected at both the short and the long echo times;
   c) selecting an arterial input function (AIF) from the $1/R2^*(t)$ data; and
   d) fitting a pharmacokinetic model to the T2/T2*-corrected short echo time data and AIF to compute selected DCE parameter maps.

6. The method of claim 1 in which step f) is performed by:
   a) computing the T2* relaxation rate at each time point $1/R2^*(t)$ from the image data signals collected at the short and long echo times;
   b) fitting a model to the $1/R2^*(t)$ data to account for confounding modifications to T2 or T2*; and
   c) creating maps of the parameters of the model that are indicators of recirculation, leakage or cellular volume fractions.

7. The method of claim 1 wherein the imaging sequence is a spiral imaging sequence.

8. The method of claim 1 wherein the imaging sequence is an echo planar imaging (EPI) sequence.

9. The method of claim 1 wherein step b) includes parallel image data acquisition methods.

10. The method of claim 1 wherein step b) comprises the acquisition of gradient echo (T2*-weighted) MRI signals.

11. The method of claim 1 wherein step b) comprises the acquisition of spin echo (T2-weighted) MRI signals.

12. The method of claim 11 wherein, the preselected permeability parameters of step g include $K_{trans}$, $v_e$ and $v_p$.

13. The method of claim 11 wherein step c) is performed by:
   a) computing the T2 relaxation rate at each time point $1/R2(t)$ from the image data signals collected at the short and long echo times;
   b) fitting a model to the $1/R2(t)$ data to account for confounding modifications to T2; and
   c) correcting the $1/R2$ data for residual T2 effects.

14. The method of claim 11 wherein step d) is performed by:
   a) computing the T2 relaxation rate at each time point $1/R2(t)$ from the image data signals collected at the short and long echo times;
   b) fitting a model to the $1/R2(t)$ data to account for confounding modifications to T2; and
   c) selecting an arterial input function (AIF) from the $1/R2(t)$ data.

15. The method of claim 11 wherein step e) is performed by:
  a) computing the T2 relaxation rate at each time point 1/R2(t) from the image data signals collected at the short and long echo times;
  b) correcting the short echo time image data signals for T2 effects using the data signals collected at both the short and the long echo times;
  c) selecting an arterial input function (AIF) from the 1/R2(t) data; and
  d) fitting a pharmacokinetic model to the T2-corrected short echo time data and AIF to compute selected DCE parameter maps.

16. The method of claim 11 in which step f) is performed by:
  a) computing the T2 relaxation rate at each time point 1/R2(t) from the image data signals collected at the short and long echo times;
  b) fitting a model to the 1/R2(t) data to account for confounding modifications to T2; and
  c) creating maps of the parameters of the model that are indicators of recirculation, leakage or cellular volume fractions.

17. The method of claim 11 wherein the imaging sequence is a spiral imaging sequence.

18. The method of claim 11 wherein the imaging sequence is an echo planar imaging (EPI) sequence.

19. The method of claim 11 wherein step b) includes parallel image data acquisition methods.

20. The method of claim 1 wherein the contrast agent of step a) is selected from a group consisting of Gd (Gadolinium)-chelated contrast agents and superparamagnetic iron-oxide contrast agents.

21. The method of claim 11 wherein the contrast agent of step a) is selected from a group consisting of Gd (Gadolinium)-chelated contrast agents and superparamagnetic iron-oxide contrast agents.

* * * * *